United States Patent [19]

Stokes et al.

[11] Patent Number: 5,443,492
[45] Date of Patent: Aug. 22, 1995

[54] MEDICAL ELECTRICAL LEAD AND INTRODUCER SYSTEM FOR IMPLANTABLE PULSE GENERATOR

[75] Inventors: Kenneth B. Stokes, Brooklyn Park; Keith J. Proctor, Lino Lakes; Rick D. McVenes, Isanti, all of Minn.

[73] Assignee: Medtronic, Inc., Minneapolis, Minn.

[21] Appl. No.: 189,565

[22] Filed: Feb. 2, 1994

[51] Int. Cl.⁶ ............................................. A61N 1/04
[52] U.S. Cl. .................................................... 607/131
[58] Field of Search ............................ 607/126–128, 607/131

[56] References Cited

U.S. PATENT DOCUMENTS

| | | | |
|---|---|---|---|
| Re. 27,990 | 10/1976 | Hon et al. | 128/2.06 E |
| 3,416,534 | 12/1968 | Quinn | 607/131 |
| 3,880,169 | 4/1975 | Starr et al. | 128/418 |
| 4,066,085 | 1/1978 | Hess | 607/131 |
| 4,299,239 | 11/1981 | Weiss et al. | 128/785 |
| 4,306,562 | 12/1981 | Osborne | 128/348 |
| 4,341,226 | 7/1982 | Peters | 128/784 |
| 4,467,817 | 8/1984 | Harris | 128/786 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,687,469 | 8/1987 | Osypka | 604/161 |
| 4,711,251 | 12/1987 | Stokes | 128/784 |
| 4,858,623 | 8/1989 | Bradshaw et al. | 128/785 |
| 4,886,065 | 12/1989 | Collins | 128/642 |
| 4,964,414 | 10/1990 | Handa et al. | 128/784 |
| 5,180,372 | 1/1993 | Vegoe et al. | 604/161 |
| 5,246,014 | 9/1993 | Williams et al. | 607/122 |

FOREIGN PATENT DOCUMENTS 3529578 2/1987 Germany ......................... 607/128

*Primary Examiner*—William E. Kamm
*Attorney, Agent, or Firm*—Michael J. Jaro; Harold R. Patton

[57] ABSTRACT

An implantable lead for establishing electrical contact between a medical device and body tissue, in which an active fixation mechanism secures the lead in place while allowing a distal electrode on the lead to mechanically "float" with respect to the body tissue. In one embodiment, the active fixation mechanism comprises a curved hook disposed on the lead at a point spaced proximally back from the distal end of the lead. The curved hook defines a helix around at least a portion of the lead's circumference. A hollow introducer needle is slidably disposed on the lead. The hollow needle provided with a longitudinal slit in a distal section of is length, such that the distal section of the needle can be advanced over the distal end of the lead, past the fixation hook, which is received in the longitudinal slit. With the needle slid over the distal end of the lead, the needle is stabbed tangentially into an implant site, bringing the fixation hook proximal to the surface of the body tissue. Then, the needle is twisted (bringing about a twisting of the lead), causing the curved fixation hook to pierce and engage the body tissue, securing the lead in place. Then the needle is withdrawn from the body tissue and removed from the lead. In an alternative embodiment, the lead can be placed by an endocardial approach using a flexible cannula with a longitudinally slotted tip.

18 Claims, 3 Drawing Sheets

MEDICAL ELECTRICAL LEAD AND INTRODUCER SYSTEM FOR IMPLANTABLE PULSE GENERATOR

FIELD OF THE INVENTION

This invention relates generally to the field of implantable medical device systems, and more particularly to an implantable medical device system which includes an electrically conductive lead.

BACKGROUND OF THE INVENTION

In the medical field, various types of implantable leads are known and used. Particularly in the field of cardiac pulse generators, the use of implanted pacing and/or sensing leads is very common. Implantable cardiac pulse generators are typically implanted either in the region of a patient's thoracic cavity, for example under the skin near the patient's left or right clavicle, or in the patient's abdomen. A pacemaker lead, having a proximal end coupled to the pulse generator and a distal end that is in electrical contact with the patient's heart muscle, functions to convey electrical cardiac signals to sensing circuitry associated with the pulse generator, and/or to convey electrical stimulating pulses (e.g., pacing pulses) to the cardiac muscle from the pulse generator.

Different types of cardiac lead configurations may be required depending upon whether implantation is to be endocardial (i.e., when the lead is transvenously introduced to place the distal end within one of the chambers of the heart) or epicardial (i.e., when the lead is introduced from the outside of the cardiovascular system to bring the distal end in contact with epicardial or myocardial tissue).

Whether a lead is configured for epicardial use or endocardial use, it is important that a mechanically stable and electrically efficient interface between cardiac tissue and the electrode(s) be established. From an electrical perspective, the electrode/tissue interface is typically characterized in terms of its threshold and its impedance. Those of ordinary skill in the art will appreciate that it is desirable to minimize the threshold of the electrode/tissue interface, so that the current drained from the pulse generator batter can be minimized by using lower-level stimulating pulses. On the other hand, it is also desirable to efficiently maximize the impedance of the electrode/tissue interface to additionally minimize the current drain.

It has been shown in the prior art that the impedance of the electrode/tissue interface can be maximized by decreasing the geometric surface area (size) of the stimulating electrode. There is a trade-off, however, between providing a small size electrode and ensuring suitable sensing and low-threshold properties of the electrode. This trade-off is discussed in greater detail in U.S. patent application Ser. No. 08/056,448 filed on Apr. 30, 1993 in the name of James T. Gates and entitled "Substrate for a Sintered Electrode," which application is hereby incorporated herein by reference in its entirety. As noted in the Gates '448 application, a considerable breakthrough in the development of low-threshold, high-impedance electrode technology occurred with the invention of a steroid-eluting porous pacing electrode, as described in U.S. Pat. No. 4,506,680 to Stokes, and related U.S. Pat. Nos. 4,577,642; 4,606,118; and 4,711,251, all commonly assigned to the assignee of the present invention and hereby incorporated by reference herein in their respective entireties.

The electrode disclosed in the Stokes '680 patent is constructed of porous, sintered platinum, titanium, or the like. Proximate the electrode is placed a plug of silicone rubber impregnated with the sodium salt of dexamethasone phosphate or other glucocorticosteroids. The silicone rubber plug allows the release of the steroid through the interstitial gaps in the porous sintered metal electrode to reach the electrode/tissue interface. The eluted steroid mitigates inflammation, irritability and subsequent excessive fibrosis of the tissue adjacent to the electrode itself.

While the steroid-eluting lead described in the Stokes '680 patent represent a significant advancement in the field of low-threshold, high-impedance cardiac leads, the mechanical attributes of the electrode/tissue interface and of the mechanism employed to ensure good fixation and permanent engagement of the lead with cardiac tissue can also have a significant impact on the threshold and impedance characteristics of a lead. Mechanical considerations are particularly relevant in the context of chronically-implanted leads, which are subjected to years of mechanical stresses.

With regard to the fixation mechanism for securing the electrode in a desired position, various approaches have been proposed in the prior art. Such mechanisms fall generally into two categories: passive fixation and active fixation. A well-known example of a passive fixation mechanism is an endocardial lead provided with pliant barbs or "tines" attached at or near the distal tip to engage the trabeculae within the heart chamber. Known active fixation mechanisms include corkscrews, hooks, piercing barbs or other anchoring structures arranged at or near the distal tip for penetration of cardiac tissue upon proper positioning of the electrode.

An example of a lead having a hook-type stab-in fixation mechanism is the Model 4951 lead manufactured by Medtronic, Inc., Minneapolis, Minn. Experimental data suggests that over time, electrodes such as the Model 4951 tend to have the myocardium between the hooked electrode and the epicardial pad replaced with fat. Such fat deposits are believed to be the result of muscle degeneration, probably an effect of the way the tissue beats against the rigid electrode. Hook-type electrodes which angle down into the myocardium (as opposed to the upward angle of the Model 4951) may provoke additional fibrotic damage at and in the tissue distal to the electrode's sharp point. Additionally, such downward-oriented hooks may also provoke fibrotic tracts angling further down under the electrode. Those of ordinary skill in the art will appreciate that such fibrotic and/or fatty deposits tend to reduce the quality of the electrode/tissue interface.

Similar fatty replacement, inflammatory, and fibrotic responses have also been observed for so-called "stab-in" type electrodes (such as the Model 5815 manufactured by Medtronic) and "screw-in" type electrodes (such as the Model 6917A manufactured by Medtronic).

For each of the active-fixation epicardial electrodes discussed above, the electrodes are applied to the epicardial surface of the heart with the electrode in intimate contact with the myocardium and held rigid with respect to the surrounding compliant myocardial tissue. Such rigidity is believed to contribute to the aforementioned fatty-replacement, inflammatory, and fibrotic responses which can result in sub-optimal electrical performance, particularly in long-term implants.

SUMMARY OF THE INVENTION

The present invention is directed to an active-fixation lead design intended to eliminate the types of perceived disadvantages in the prior art, in particular, the complications resulting from tissue reaction to immobile electrodes in the contractile planes of the tissue.

In a preferred embodiment of the invention, an electrode configuration having a small-surface porous platinized steroid-eluting platinum electrode is employed. The entire electrode assembly, which is disposed at the distal end of the lead, is preferably made as small as possible (for example, on the order of 0.028-inches in diameter, and 0.25-inches or shorter in length). The lead body is preferably as supple a design as possible, utilizing, in a preferred embodiment, a two-strand bundle-stranded wire (BSW) conductor with small diameter urethane tubing insulation.

In accordance with one embodiment of the invention, the electrode assembly includes an active fixation mechanism which allows the electrode assembly to "float" with respect to the surrounding myocardial tissue, thereby provoking a minimum of inflammatory and mechanical tissue reaction. In particular, the active fixation mechanism comprises a fixation hook disposed at a point spaced back from the extreme distal end of the lead. The hook is configured such that it extends radially outward from the lead for a short distance and then coils helically around at least a portion of the lead's circumference.

In accordance with one aspect of the present invention, the full benefits of local steroid therapy can be realized, allowing the small-surface electrode to provide low threshold, high impedance performance demonstrated in conventional endocardial designs. It is believed that the present invention thereby offers advantages over conventional rigid epicardial active fixation mechanisms.

Application of the active-fixation lead in accordance with the present invention involves making a small oblique (tangential) stab wound into the heart tissue epicardium and inserting the distal electrode assembly into the stab wound. In a preferred embodiment of the invention, the method of application involves the use of a hollow, splittable needle having a longitudinal slit along a portion of its distal end to accommodate the helical needle fixation mechanism. The splittable needle is configured to be slidably disposed along the lead body. When the splittable needle is advanced toward the distal end of the lead, the portion of the coiled fixation hook which extends radially outward from the lead is received within and slides along the longitudinal slit in the splittable needle. The longitudinal slit extends back from the distal end of the splittable needle for a distance at least as long as the distance on the lead between the fixation hook and the distal end of the electrode. This allows the extreme distal end of the electrode assembly to be retracted completely within the distal end of the splittable needle when the splittable needle is fully advanced distally along the lead.

When the distal end of the electrode assembly is fully retracted within the distal end of the hollow needle, the needle is then inserted into the myocardium at the desired stimulation site. In particular, the needle is preferably inserted far enough into the myocardium that the fixation hook on the lead becomes positioned proximate to the surface of the myocardium. The splittable needle and lead are then twisted, so that the helically coiled fixation hook itself pierces the epicardium and becomes engaged in the myocardium. Then, the splittable needle is withdrawn along the lead body, leaving the electrode and fixation hook in place. The needle is then removed from the lead body by splitting it apart.

In another embodiment of the invention, a hollow cylindrical sheath extending along substantially the entire length of the lead is substituted for the hollow needle, enabling the lead to be implanted transvenously, with the aid of a guide catheter of sufficient diameter to receive the lead and sheath therein. The sheath is provided with a slit at its distal end similar to the slit in the hollow needle, such that once the distal end of the lead is positioned at the desired fixation site within the heart, twisting the sheath causes the rotation of the lead necessary for the helical hook to pierce the endocardium and engage the myocardium.

BRIEF DESCRIPTION OF THE DRAWINGS

The above-described and other aspects of the present invention may be better understood and appreciated with reference to a detailed description of a specific embodiment of the invention, when read in conjunction with the accompanying drawings, wherein.

The drawings are not necessarily to scale.

DETAILED DESCRIPTION OF A SPECIFIC EMBODIMENT OF THE INVENTION

Figure 1:
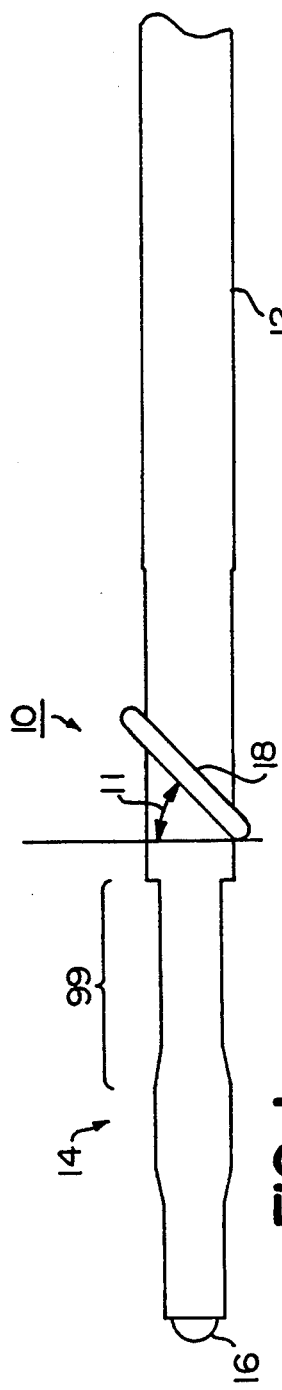
FIG. 1 is a greatly enlarged side view of a distal portion of a lead and electrode assembly in accordance with one embodiment of the invention.

Referring to FIG. 1, there is shown a greatly enlarged side view of a lead 10 in accordance with one embodiment of the present invention. Lead 10 comprises an elongate lead body 12 and a tip electrode assembly, designated generally by reference numeral 14 in FIG. 1, disposed at the distal end of lead body 12. (Only a distal section of elongate lead body 12 is shown in FIG. 1.)

In the presently preferred embodiment, tip electrode assembly 14 is generally of the porous platinized type described in detail in the above-referenced Gates '448 application and in U.S. patent application Ser. No. 08/146,265 filed on Oct. 29, 1993 in the name of Gary R. Schildgen and entitled "Medical Electrical Lead and Method of Manufacture," which application is hereby incorporated by reference herein in its entirety.

Figure 2:
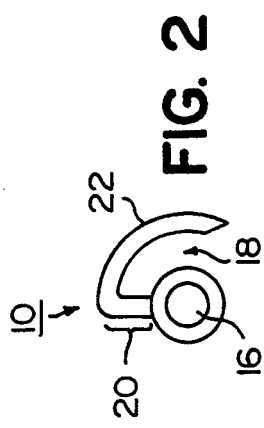
FIG. 2 is a greatly enlarged end view of the distal portion of the lead and electrode assembly from FIG. 1.

With continued reference to FIG. 1, there is disposed on lead 10 at a point spaced back from the extreme distal porous platinized tip electrode 16 a helically coiling hook 18 whose configuration can perhaps be better appreciated with reference to the enlarged end view of lead 10 shown in FIG. 2. As shown in FIG. 2, hook 18 is coupled at its proximal end to lead 10 and includes a section 20 which projects radially outward with respect to the longitudinal axis of lead 10. Another portion 22 of hook 18 curves around a portion of the circumference of the lead 10.

Curved portion 22 of hook 18 shown in FIG. 2 angles back toward the proximal end of lead 10, giving curved portion 22 a substantially helical configuration. In particular, the helix defined by curved portion 22 of hook 18 spirals about the central longitudinal axis of lead 10, around at least a portion of the circumference of lead 10. In the presently preferred embodiment of the invention, curved portion 22 of hook 18 is preferably oriented at approximately 45° with respect to the longitudinal axis of lead 10 as represented by angle 11 in FIG. 1. It is believed that such an angled configuration of curved portion 22 of hook 18 facilitates introduction of lead 10 into an implantation site, and further facilitates and enhances the fixation of lead 10.

Figure 3:
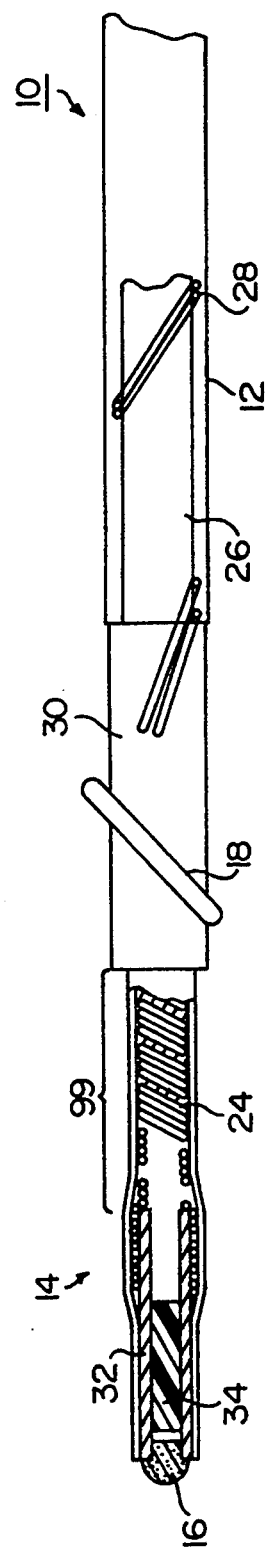
FIG. 3 is a greatly enlarged, partially cut-away cross-sectional view of the distal portion of the lead and electrode assembly form FIG. 1.

Turning now to FIG. 3, there is shown a greatly enlarged, partially cross-sectional view of the distal end portion of lead 10 in accordance with the presently disclosed embodiment of the invention. In accordance with the presently disclosed embodiment of the invention, lead 10 is of the bipolar type, having two separate conductors and two separate electrodes. In particular, a first, inner conductor 24 extends along the length of lead body 12 and is electrically coupled to tip electrode 16 at the distal end of tip electrode assembly 14. Conductor 24 may be, for example, four strands of bundle-stranded wire (BSW), although any other suitable configuration for a conductor may be used, such as a coiled conductor. Throughout the length of lead 10, inner conductor 24 is surrounded by thin, small diameter polyurethane or silicone rubber tubing 26, which insulates conductor 24 from a two-strand second BSW outer conductor 28. Outer conductor 28 extends along the length of lead 10 and is electrically coupled to hook 18. Specifically, the electrical coupling of outer conductor 28 is accomplished through resistance spot welding (or laser welding, crimping, or the like) to a stainless steel cylindrical core 30 which itself is disposed between lead body 12 and tip electrode assembly 14. Fixation hook 18 is also coupled to core 30, such that hook 18 serves as one of the two electrodes of bipolar lead 10.

Although lead 10 in accordance with the disclosed embodiment is of the bipolar type, in which hook 18 serves as both the fixation mechanism and one of the electrodes, it is contemplated that a lead in accordance with the present invention could be of the unipolar type, in which hook 10 serves as the fixation mechanism but not as an electrode. Moreover, it is contemplated that a lead in accordance with the present invention could have any number of electrodes, as required for a particular application, and it is believed that those of ordinary skill in the art having the benefit of the present disclosure would be readily able to adapt the embodiment described herein accordingly.

With continued reference to FIG. 3, tip electrode assembly 14 includes distal tip electrode 16 which is depicted as a porous platinum generally hemispherical object (which may additionally be covered with platinum black) at the end of a cylindrical substrate member 32. Although platinum or a platinum alloy (such as platinum/iridium) is the preferred material for electrode 16 and substrate 32, they may additionally include or be made entirely from various other materials, including (but not limited to) such materials as palladium, titanium, tantalum, rhodium, iridium, carbon, vitreous carbon and alloys, oxides and nitrides of such metals, or other conductive materials. Electrode 16 in accordance with the presently disclosed embodiment is manufactured from a viscous slurry mixture of platinum splat powder and an organic binder. The manner in which electrode assembly 16 may be manufactured is described in greater detail in the above-referenced Schildgen and Gates patent applications.

Tip electrode assembly 14 further includes a steroid-silicone compound element 34 disposed within substrate 32. Steroid-silicone compound element 34 forms a monolithic controlled release device when it is loaded with an anti-inflammatory agent, e.g., a steroid, dexamethasone sodium phosphate. The steroid also is deposited within the pores of electrode 16 by application of a solution of dexamethasone sodium phosphate, isopropanol and distilled or deionized water. This process is described in greater detail in the above-referenced Schildgen and Gates patent applications, as well as in the above-referenced Stokes patents.

In a preferred embodiment, tip electrode 16 has a macroscopic surface area (size) of 4.0-mm$^2$ or less exposed to body tissue or fluids. As shown in FIG. 3, the exposed surface of electrode 16 is generally hemispherical. The small geometric macroscopic electrode size is intended to produce the desired very high pacing impedance. The porous surface configuration together with platinum black electroplating contribute to a microscopically large surface area for low polarization, low source impedance and low thresholds. The porous surface also facilitates the elution of steroid and adhesion of the platinum black to the electrode surface. Electrode 16 thus permits steroid to elute therethrough.

With continued reference to FIG. 3, inner conductor 24 is electrically coupled to the proximal end of substrate 32. Inner insulative polyurethane tubing 26 extends along the entire length of lead body 12 and electrode assembly 14, leaving exposed only tip electrode 16 at the extreme distal end of electrode assembly 14. As can be appreciated from inspection of the FIGS. region 99 of lead body 12 between distal electrode 16 and fixation hook 18 is flexible. As such electrode 16 may readily move and conform to the contractile movement of the heart tissue, i.e. "float", once it has been inserted.

Figure 4:
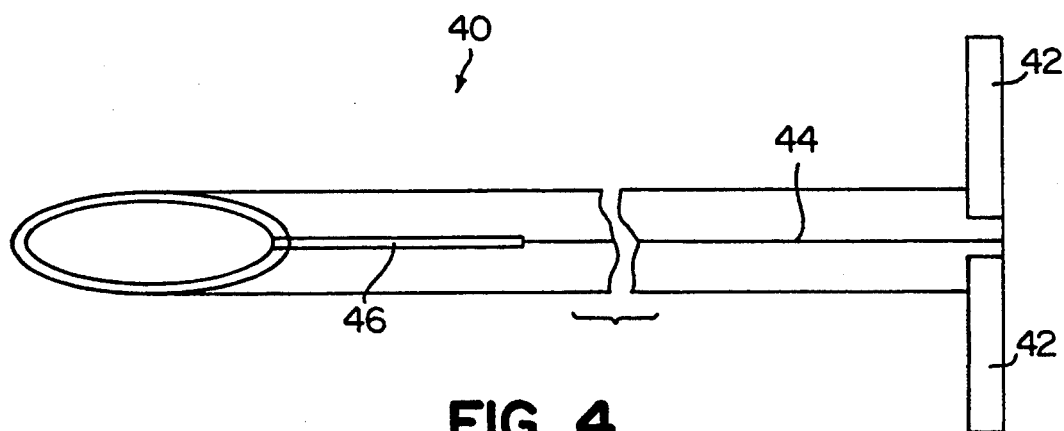
FIG. 4 is a greatly enlarged view of a needle used for introduction and fixation of the lead and electrode assembly from FIG. 1.

Turning now to FIG. 4, there is shown a greatly enlarged view of a splittable needle 40 used for insertion and fixation of lead 10 in accordance with the presently disclosed embodiment of the invention. Splittable needle 40 has an inner diameter sufficient to allow it to be slidably disposed around lead 10. At the proximal end of needle 40, tabs 42 are provided for facilitating the splitting apart of needle 40 along a score 44 therein which extends along the entire length of needle 40. Score 44 may be made in any manner known in the art for providing a weakened line along which needle 40 may be split, including scribing, perforating, and the like. Splittable needles as thus far described are well-known and commercially available, for example from Luther Medical Corporation, Tustin, Calif. In addition if an introducer is fashioned from a polymer it may also be made removable through use of a orientated polymer, such as an extruded TEFLON, which permits the introducer to be torn in a longitudinal direction, discussed for example in U.S. Pat. No. 4,306,562 to Osborne; providing a line of material weakened in a longitudinal direction as shown in Vegoe et al U.S. Pat. No. 5,180,372, both of which are incorporated herein by reference. Other introducers may also be used which are severable by means of a slitter, for example as shown in the U.S. Pat.

No. 4,687,469 to Osypka, incorporated herein by reference. In addition although provision of a score-line is the preferred manner to accomplish removal of needle 40 from lead 10, any other additional known manner may be provided to permit removal of the introducer needle or cannula from the lead without requiring the introducer needle or cannula to be removed over an end of the lead.

Figure 5:
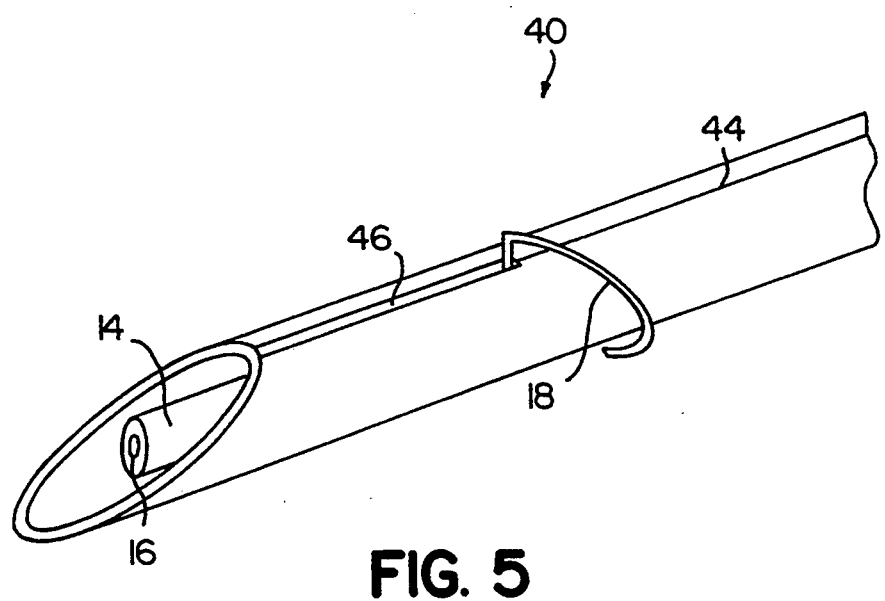
FIG. 5 is a greatly enlarged perspective view of the distal end of the needle from FIG. 4 disposed around the lead and electrode assembly from FIG. 1.

In addition to longitudinal score 44, needle 40 is provided with a slit 46 along a distal section thereof. In accordance with the presently disclosed embodiment of the invention, when needle 40 is advanced toward the distal end of lead 10 (and in particular, when tip electrode assembly 14 is retracted within the distal end of needle 40), fixation hook 18 on electrode assembly 14 is received into and slides along slit 46. As shown in FIG. 5, this allows electrode assembly 12 to be completely retracted within the lumen of needle 40. That is, needle 40 can be advanced forward along lead 10 such that the distal end of needle 40 extends beyond hook 18 on electrode assembly 12.

To introduce and affix lead 10 in accordance with the present invention, needle 40 is advanced to the forward (distal) position depicted in FIG. 5, wherein electrode assembly 14 is disposed within the lumen of needle 40. Needle 40 is then inserted into an appropriate entry site, for example, a subxyphoid site which provides access to epicardial tissue. The distal end of needle 40 is stabbed obliquely (tangentially) into the desired epicardial site, and in particular is inserted into the myocardial tissue to the point where hook 18 is situated proximal to the tissue surface. Next, needle 40 is rotated about its longitudinal axis. This rotation is facilitated by tabs 42. Since hook 18 is engaged within slit 46 in needle 40, rotation of needle 40 brings about rotation of lead 10 as well. As a result of such rotation, hook 18 pierces the epicardial tissue and becomes engaged therein. Since hook 18 is spaced back from the extreme distal end of electrode assembly 12, however, and region 99 of lead body 12 is flexible, electrode 16 is not rigidly attached to cardiac tissue, but instead is left essentially "floating" with the compliant cardiac tissue.

Once hook 18 has completely engaged the cardiac tissue through rotation of needle 40, needle 40 is withdrawn toward the proximal end of lead 10, leaving electrode assembly 14 and hook 18 undisturbed. Because connectors and the like disposed on the proximal end of lead body 12 would prevent complete removal of needle 40, needle 40 is simply split apart and discarded.

Figure 6:
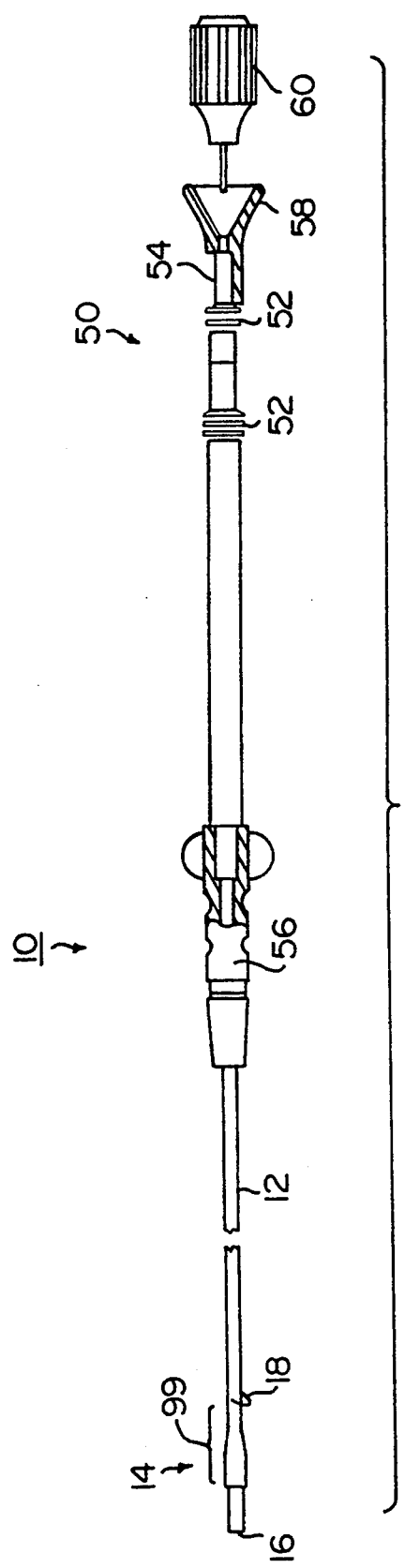
FIG. 6 is a plan view of the lead from FIG. 1 shown both the proximal and distal ends thereof.

Turning now to FIG. 6, there is shown a plan view of lead 10 constructed in accordance with the presently disclosed embodiment of the invention. As previously noted, lead body 12 is covered by an insulative sleeve of flexible biocompatible and biostable insulating material, such as polyurethane or silicone rubber. At the proximal end of lead 10, a terminal assembly designated generally as 50 is provided for coupling lead 10 to an implantable pulse generator (not shown). Terminal assembly 50 is provided with sealing rings 52 and a terminal pin 54, all of a type known in the art. An anchoring sleeve 56 (shown partially in cross-section) may also be provided on lead body 12. As would be familiar to those of ordinary skill in the art, anchoring sleeve 56 slides over lead body 12 and serves as a point for suturing lead body 12 to body tissue at the insertion point of lead 10 in a fashion known in the art. Anchoring sleeve 56 and terminal assembly 50 are preferably fabricated from silicone rubber, although they may also be constructed of any other suitable biocompatible material known in the art.

Lead 10 as shown in FIG. 6 further may also include a stylet guide 58 and stylet assembly 60 coupled to terminal pin 54 for imparting stiffness to lead 10 during the insertion and placement of lead 10. Stylet guide 58 and stylet assembly 60 are discarded after use and before connection of terminal pin 54 to a pacemaker pulse generator.

As will be appreciated by those of ordinary skill in the art, it is the presence of terminal assembly 50 (and anchoring sleeve 56, if provided) which necessitates the use of a needle 40 which is splittable, as previously described. That is, since the larger diameter of terminal assembly 50 (and anchoring sleeve 56) with respect to the diameter of lead body 12 prevents needle 40 from being withdrawn off of the proximal end of lead 10, needle 40 must be split apart at some point along the length of lead body 12.

From the foregoing detailed description of a specific embodiment of the invention, it should be apparent that a lead and electrode assembly having a helical hook active fixation mechanism disposed at a point spaced back from the distal end of the lead and electrode assembly has been disclosed. Although a specific embodiment of the invention has been disclosed in some detail, this has been done for the purposes of illustration only, and is not intended to be limiting with regard to the scope of the invention. It is contemplated that various substitutions, alterations, and/or modifications, including but not limited to those specifically discussed herein, can be made to the disclosed embodiment without departing from the spirit and scope of the invention as defined in the appended claims, which follow.

What is claimed is:

1. An implantable lead for establishing electrical contact between a medical device and body tissue, comprising:
   an elongated lead body having proximal and distal ends and having at least one electrical conductor extending between said proximal and distal ends;
   a terminal assembly disposed on said proximal end of said lead body;
   an electrode assembly disposed proximate said distal end of said lead body, said electrode assembly including a first electrode, said first electrode electrically connected to said conductor;
   a curved fixation hook disposed on said lead body, said curved fixation hook disposed at a point spaced back from said distal end of said lead and extends radially outward from said lead for a first distance and then coiling around at least a portion of said lead's circumference.

2. A lead in accordance with claim 1, wherein said curved fixation hook extends radially outward from said lead body at a first angle with respect to a longitudinal axis of said lead body.

3. The lead in accordance with claim 2 wherein said first direction is less than ninety degrees.

4. A lead in accordance with claim 1, wherein said first electrode is disposed at the distal end of said lead body.

5. A lead in accordance with claim 1, wherein said fixation hook is coupled to said at least one conductor, such that said fixation hook comprises an electrode of said lead.

6. A lead and introducer system in accordance with claim 1, wherein said electrode assembly further comprises a steroid-silicone compound element disposed within said electrode assembly.

7. A lead and introducer system, comprising:
an elongated lead body having proximal and distal ends and having at least one electrical conductor extending between said proximal and distal ends;
a terminal assembly disposed on said proximal end of said lead body;
an electrode assembly, disposed at the distal end of said lead body, said electrode assembly including a first electrode disposed at the distal end thereof, said first electrode electrically connected to said conductor;
a curved fixation hook, disposed on said lead at a point spaced back from said first electrode said curved fixation hook extends radially outward from said lead for a first distance and then coils around at least a portion of said lead's circumference;
a hollow introducer needle, disposed around said lead body, said needle having a longitudinal slit formed in a distal section of said needle.

8. A lead and introducer system in accordance with claim 7, wherein said introducer needle is provided with a longitudinal score to facilitate splitting apart said needle upon introduction and fixation of said lead.

9. A lead and introducer system in accordance with claim 7, wherein said curved fixation hook extends radially outward from said lead body at a first angle with respect to a longitudinal axis of said lead body, said first angle is less than ninety degrees.

10. An implantable lead and introducer system, comprising:
an elongate, flexible lead body having proximal and distal ends and having at least one electrical conductor extending between said proximal and distal ends;
an electrode assembly, disposed at the distal end of said lead body, said electrode assembly including a first electrode disposed at the distal end thereof, said first electrode electrically connected to said conductor
a fixation hook, disposed on said lead at a point spaced back from said first electrode, said fixation hook configured to curve around at least a portion of said lead's circumference and adapted to engage said body tissue upon rotation of said lead;
an introducer cannula, slidably disposed on said lead body, said cannula having a longitudinal slit formed in a distal section thereof, said slit allowing said distal section of said needle to be slid distally beyond said fixation hook and over said electrode assembly.

11. A lead and introducer system in accordance with claim 10, wherein said cannula is provided with a means for permitting removal of said cannula from said lead without requiring said cannula to be removed over an end of said lead, to facilitate splitting apart said cannula upon introduction and fixation of said lead.

12. A lead and introducer system in accordance with claim 11, wherein said means for permitting removal comprise a longitudinal score line.

13. A lead and introducer system in accordance with claim 16, wherein said curved fixation hook extends radially outward from said lead body at a first angle with respect to a longitudinal axis of said lead body, said first angle is less than ninety degrees.

14. A medical electrical lead and introducer system comprising:
a terminal assembly;
a lead body having a conductor and insulative sleeve, the lead body further having a longitudinal axis, the conductor having a first end and a second end, the first end coupled to the terminal assembly, the insulative sleeve insulting an outer surface of the conductor between the first end and the second end;
an electrode coupled to the second end of the conductor;
a fixation hook having a first portion and a second portion, the first portion extending in a direction radial to the lead body, the first portion attached to the lead body at an angle to the longitudinal axis, the second portion attached to the first portion and curved; and
a hollow introducer sheath disposed over the lead body, electrode and fixation hook, the hollow introducer sheath having a slot at a distal end and a score line, the slot and the score line being collinear, the slot being greater in width than the first portion of the fixation hook.

15. A lead in accordance with claim 14, wherein the longitudinal slit extends proximal from the distal end of the sheath a first distance, the first portion is attached to the lead body at a second distance proximal from the electrode, the first distance being at least as great as the second distance.

16. A lead in accordance with claim 14, wherein the sheath comprises a hollow needle.

17. A medical electrical lead and introducer system comprising:
a terminal assembly;
a lead body having a conductor and insulative sleeve, the lead body further having a longitudinal axis, the conductor having a first end and a second end, the first end coupled to the terminal assembly, the insulative sleeve insulting an outer surface of the conductor between the first end and the second end;
an electrode coupled to the second end of the conductor;
a curved fixation hook attached to the lead body at a first angle to the longitudinal axis; and
a hollow introducer sheath disposed over the lead body, electrode and fixation hook, the hollow introducer sheath having a slot at a distal end and a score line, the slot and the score line being collinear, the slot being greater in width than the width of the fixation hook.

18. A lead in accordance with claim 17, wherein the sheath comprises a hollow needle.

* * * * *